US012741916B2

(12) United States Patent
Kucmierczyk et al.

(10) Patent No.: US 12,741,916 B2
(45) Date of Patent: Sep. 22, 2026

(54) PROCESS FOR PROVIDING A STREAM COMPRISING A HIGH PROPORTION OF 2,4,4-TRIMETHYLPENT-1-ENE

(71) Applicant: Evonik Oxeno GmbH & Co. KG, Marl (DE)

(72) Inventors: Peter Kucmierczyk, Herne (DE); Robert Franke, Marl (DE); Anna Chiara Sale, Duesseldorf (DE); Dirk Fridag, Haltern am See (DE); Ana Markovic, Haltern am See (DE); Armin Matthias Rix, Marl (DE); Maren Termühlen, Dortmund (DE); Laura-Selin Harding, Dorsten (DE); Jan Benedikt Metternich, Recklinghausen (DE)

(73) Assignee: Evonik Oxeno GmbH & Co. KG, Marl (DE)

( * ) Notice: Subject to any disclaimer, the term of this patent is extended or adjusted under 35 U.S.C. 154(b) by 208 days.

(21) Appl. No.: 18/738,400

(22) Filed: Jun. 10, 2024

(65) Prior Publication Data

US 2024/0417346 A1 Dec. 19, 2024

(30) Foreign Application Priority Data

Jun. 14, 2023 (EP) .................................... 23179201

(51) Int. Cl.

*C07C 5/23* (2006.01)
*C07C 5/22* (2006.01)
*C07C 5/25* (2006.01)

(52) U.S. Cl.

CPC ........ *C07C 5/2568* (2013.01); *C07C 2529/06* (2013.01); *C07C 2531/10* (2013.01)

(58) Field of Classification Search

CPC .............. C07C 5/2568; C07C 2529/06; C07C 2531/10; C07C 2529/04; C07C 5/2518;

(Continued)

(56) References Cited

U.S. PATENT DOCUMENTS 2,554,251 A 5/1951 Hudson, Jr.
3,308,069 A 3/1967 Wadlinger et al.

(Continued)

FOREIGN PATENT DOCUMENTS

CN 113198519 8/2021
DE 10 2006 040 433 3/2008

(Continued)

OTHER PUBLICATIONS

European Search Report dated Dec. 4, 2023, in European Patent Application No. 23179201.1, 7 pages.

(Continued)

*Primary Examiner* — Tam M Nguyen
(74) *Attorney, Agent, or Firm* — Grüneberg Global IP, PLLC

(57) ABSTRACT

A process provides a tops stream K containing more than 85% by weight of 2,4,4-trimethylpent-1-ene, wherein both an isomerization of 2,4,4-trimethylpont-2-ene to 2,4,4-trimethylpont-1-ene and a distillation to obtain the tops stream K are performed. The isomerization is at least partially fed with the bottoms stream of the distillation where a tops stream K is withdrawn overhead.

20 Claims, 3 Drawing Sheets

(58) Field of Classification Search
CPC ......... C07C 7/04; C07C 5/222; C07C 5/2273; C07C 11/02; C07C 2529/70
See application file for complete search history.

(56) References Cited

U.S. PATENT DOCUMENTS

| | | | | |
|---|---|---|---|---|
| 3,326,866 | A | 6/1967 | Haag | |
| 3,454,668 | A * | 7/1969 | Downs | C07C 5/2781 585/747 |
| 4,992,613 | A | 2/1991 | Brownscombe | |
| 6,875,901 | B2 * | 4/2005 | Gartside | C07C 5/2512 585/668 |
| 7,002,053 | B2 | 2/2006 | Nierlich et al. | |
| 2003/0100811 | A1 * | 5/2003 | Dakka | C07C 2/12 585/533 |
| 2004/0097773 | A1 | 5/2004 | Beckmann et al. | |
| 2004/0122278 | A1 | 6/2004 | Powers | |
| 2008/0058572 | A1 | 3/2008 | Fernandez et al. | |
| 2024/0417345 | A1 * | 12/2024 | Kucmierczyk | C07C 5/2568 |

FOREIGN PATENT DOCUMENTS

| | | |
|---|---|---|
| EP | 1 360 160 | 3/2009 |
| WO | 2022/144208 | 7/2022 |

OTHER PUBLICATIONS

Kucmierczyk et al., U.S. Appl. No. 18/738,261, filed Jun. 10, 2024.
Kucmierczyk et al., U.S. Appl. No. 18/739,543, filed Jun. 11, 2024.
Kucmierczyk et al., U.S. Appl. No. 18/739,485, filed Jun. 11, 2024.
Kucmierczyk et al., U.S. Appl. No. 18/739,433, filed Jun. 11, 2024.
Kucmierczyk et al., U.S. Appl. No. 18/739,599, filed Jun. 11, 2024.
U.S. Appl. No. 18/738,261, filed Jun. 10, 2024, Kucmierczyk et al.
U.S. Appl. No. 18/739,543, filed Jun. 11, 2024, Kucmierczyk et al.
U.S. Appl. No. 18/739,485, filed Jun. 11, 2024, Kucmierczyk et al.
U.S. Appl. No. 18/739,433, filed Jun. 11, 2024, Kucmierczyk et al.
U.S. Appl. No. 18/739,599, filed Jun. 11, 2024, Kucmierczyk et al.
Office Action received for U.S. Appl. No. 18/738,261, mailed on Feb. 26, 2026, 22 pages.

* cited by examiner

FIG. 1

Temperature (C)
Pressure (bar)

FEED
101.7
1.00

1
2
3
4

S1
63.5
0.30

S2
67.0
0.30

SB
55.0
1.00

S4
55.0
1.00

SA
55.0
1.00

PURG
55.0
1.00

PROCESS FOR PROVIDING A STREAM COMPRISING A HIGH PROPORTION OF 2,4,4-TRIMETHYLPENT-1-ENE

CROSS-REFERENCE TO RELATED APPLICATIONS

This patent application is based on and claims priority pursuant to 35 U.S.C. § 119(a) to European Patent Application No. 23179201.1, filed on Jun. 14, 2023, in the European Patent Office, the entire disclosure of which is hereby incorporated by reference herein.

BACKGROUND

Field of the Invention

The present invention relates to a process for providing a tops stream K containing more than 85% by weight of 2,4,4-trimethylpent-1-ene, wherein both an isomerization of 2,4,4-trimethylpent-2-ene to 2,4,4-trimethylpent-1-ene and a distillation to obtain the tops stream K are performed. The isomerization is at least partially fed with the bottoms stream of the distillation where a tops stream K is withdrawn overhead.

Description of Related Art

Diisobutene is an industrially relevant product obtained by dimerization of isobutene. Diisobutene consists of the isomers 2,4,4-trimethylpent-1-ene (hereinbelow also: TMP1) and 2,4,4-trimethylpent-2-ene (hereinbelow also: TMP2) with a mass distribution of TMP1: TMP2 of about 78:22 to 81:19 (equilibrium distribution). This mixture can be converted into higher-value products inter alia in carbonylation processes. Especially in carbonylation processes, such as methoxycarbonylation (reaction product here is methyl 3,5,5-trimethylhexanoate) or hydroformylation (reaction product here is 3,5,5-trimethylhexanal), the internal olefin TMP2 exhibits markedly lower reactivity than the terminal olefin TMP1. As a consequence of inadequate stability of the catalysts or economic factors (for example the size of the reactor), it is often not possible to adjust the reaction conditions or residence times in these carbonylation reactions sufficiently to allow the terminal TMP2 to react to completion.

A direct use of the unreacted TMP2 is disadvantageous for reasons of reactivity. It is therefore advantageous to convert the TMP2 or a portion thereof into the more reactive form TMP1 by isomerization in order ultimately to allow conversion into valuable products.

Processes for isomerization of TMP2 to TMP1 are known in the literature. However, these processes are performed under homogeneous catalysis and based on strong mineral acids such as for example $H_2SO4$, $H_3PO_4$ or benzenesulfonic acid (cf. U.S. Pat. No. 2,554,251 A). However, homogeneously catalyzed reaction systems have the disadvantage that the isomerization catalysts must be removed again from the obtained pure TMP1 or the obtained TMP1/TMP2 mixtures in a costly and inconvenient manner. Only then could they be supplied to the aforementioned carbonylation processes. Acidic systems are generally also corrosive, thus requiring high-quality materials.

A further problem is that the proportion of TMP1 in the product stream of the isomerization may still be too low, according to the downstream process step, for example a carbonylation process, to be able to achieve advantageous results in the respective downstream process step.

SUMMERY OF THE INVENTION

It is accordingly an object of the present invention to provide a process for isomerization of 2,4,4-trimethylpent-2-ene to 2,4,4-trimethylpent-1-ene which does not exhibit the aforementioned problems. The process should continuously provide a stream comprising a high proportion of 2,4,4-trimethylpent-1-ene. The process should simultaneously provide the option of converting further 2,4,4-trimethylpent-2-ene to 2,4,4-trimethylpent-1-ene.

This object was achieved by the process of the invention described herein. Preferred embodiments are also specified.

BRIEF DESCRIPTION OF THE DRAWINGS

FIG. 1 shows the flow diagram on which the simulations in example 2 have been based and which is explained in the experimental description.

DETAILED DESCRIPTION OF THE INVENTION

Figure 2:
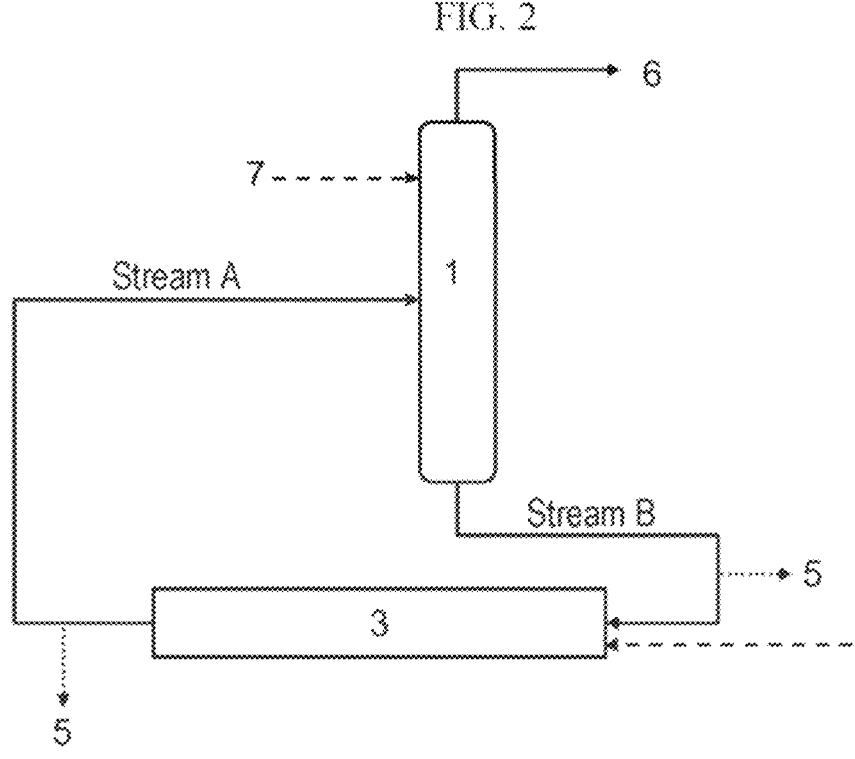
FIG. 2 shows the embodiment in which stream B is withdrawn from the distillation (1) as a bottoms stream.

According to the invention the process is a process for providing a tops stream K containing more than 85% by weight of 2,4,4-trimethylpent-1-ene, preferably more than 90% by weight of 2,4,4-trimethylpent-1-ene, particularly preferably more than 95% by weight of 2,4,4-trimethylpent-1-ene, wherein the process comprises at least the following steps:

a. supplying a stream A containing 2,4,4-trimethylpent-2-ene and 2,4,4-trimethylpent-1-ene to a distillation unit and separating the stream A into at least the tops stream K enriched in 2,4,4-trimethylpent-1-ene relative to stream A and containing more than 85% by weight of 2,4,4-trimethylpent-1-ene, preferably more than 90% by weight of 2,4,4-trimethylpent-1-ene, particularly preferably more than 95% by weight of 2,4,4-trimethylpent-1-ene, and a stream B which is depleted in 2,4,4-trimethylpent-1-ene relative to stream A;

b. performing an isomerization of 2,4,4-trimethylpent-2-ene to 2,4,4-trimethylpent-1-ene with stream B using a heterogeneous catalyst based on a zeolite or an ion-exchange resin to obtain a product stream of the isomerization in which the proportion of 2,4,4-trimethylpent-2-ene is lower and the proportion of 2,4,4-trimethylpent-1-ene is higher than in stream B; wherein the product stream of the isomerization is at least partially sent to the distillation as stream A and wherein an input stream with which the process is fed and which contains 2,4,4-trimethylpent-2-ene and 2,4,4-trimethylpent-1-ene is sent to the distillation unit in step a. in addition to stream A and/or to the isomerization in step b. in addition to stream B.

The advantage of the process according to the invention is the use of a heterogeneous catalyst system. Such a catalyst system need not be removed from the product stream but remains in the reaction vessel/the reactor. The catalyst systems according to the invention based on a zeolite or on an ion-exchange resin also allow high conversions to be achieved.

A further advantage of the process is the distillation arranged downstream of the isomerization which makes it possible to further increase the proportion of 2,4,4-trimethylpent-2-ene and 2,4,4-trimethylpent-1-ene in the tops stream K of the at least one distillation column relative to the employed stream. It is thus possible to achieve proportions of more than 85% by weight, preferably more than 90% by weight, particularly preferably more than 95% by weight, of 2,4,4-trimethylpent-1-ene in the stream, which is advantageous for downstream process steps, for example carbonylation processes.

A further advantage is the flexible supply of the input mixture. This allows the process according to the invention to be adapted to the particular circumstances, for example according to the employed input stream. If the proportions of 2,4,4-trimethylpent-2-ene and 2,4,4-trimethylpent-1-ene in the input stream are close to the equilibrium distribution, the stream may initially be sent to the distillation. If the proportions of 2,4,4-trimethylpent-2-ene and 2,4,4-trimethylpent-1-ene in the input stream differ from the equilibrium distribution, the stream could initially be sent to the isomerization. Incorporation into existing production plants is thus more easily possible according to the composition of the input stream.

Step a. of the process of the invention relates to the distillation of stream A which contains 2,4,4-trimethylpent-2-ene and 2,4,4-trimethylpent-1-ene. Stream A is separated into at least the tops stream K which is enriched with 2,4,4-trimethylpent-1-ene relative to stream A and contains more than 85% by weight of 2,4,4-trimethylpent-1-ene, preferably more than 90% by weight of 2,4,4-trimethylpent-1-ene, particularly preferably more than 95% by weight of 2,4,4-trimethylpent-1-ene, and a stream B which is depleted in 2,4,4-trimethylpent-1-ene relative to stream A.

According to the invention, stream A, which feeds the distillation, derives from the isomerization. The stream obtained as product stream in the isomerization is at least partially or completely sent to the distillation as stream A. It is possible according to the invention that in addition to stream A an input stream which feeds the process and contains 2,4,4-trimethylpent-2-ene and 2,4,4-trimethylpent-1-ene is sent to the distillation unit in step a. It is likewise possible for the input stream to be sent to the isomerization in step b. or for the input stream to be sent both to the distillation in step a. and to the isomerization in step b.

The input stream to be employed contains 2,4,4-trimethylpent-2-ene and 2,4,4-trimethylpent-1-ene. Such streams may be diisobutene streams producible by dimerization from isobutene or isobutene-containing hydrocarbon mixtures as disclosed in EP 1 360 160 B1 for example. In addition, the streams to be employed here may be obtained as unreacted residual streams in carbonylation processes, for example in methoxycarbonylation or in hydroformylation.

It has already been mentioned that the input stream can be supplied to the isomerization and/or to the distillation. The designation of steps a. and b. in the present description therefore does not constitute a prioritization or chronology. It will be apparent that both steps must be carried out and that the individual steps are fed from the respective other step. Which step is therefore considered to be carried out first is therefore of secondary importance.

The distillation in step a. of the process according to the invention is performed in a distillation unit. Corresponding units are known in principle to those skilled in the art. The distillation unit of the present invention comprises preferably at least one distillation column, more preferably at least two distillation columns. The following description of features of the distillation column also applies whenever there is more than one distillation column in the distillation unit.

The distillation column preferably comprises internals to accomplish the separation task. Appropriate internals are familiar to those skilled in the art. Particularly suitable here are random or structured packings, such as those known to those skilled in the art under trade names such as MellaPak®, MellapakPlus®, Flexipac®, etc. In a preferred embodiment of the present invention, the at least one distillation column comprises at least 50 theoretical plates, preferably at least 70 theoretical plates, more preferably at least 90 theoretical plates. If two or more distillation columns are present, the distillation columns may have an identical or different number of theoretical plates.

The operating parameters of the distillation column are oriented to the separation task and the design of the distillation column. In the present process, it is preferable that the at least one distillation column is operated at subatmospheric pressure, particularly preferably at a pressure of 0.2 to 0.9 bar. In the context of the present invention subatmospheric pressure is present whenever operations are carried out below the ambient pressure of about 1 bar, i.e. the atmospheric pressure present at the respective site. If there are two or more distillation columns, the distillation columns may be operated at the same or different pressure.

It is additionally preferable when the temperature in the bottom of the at least one distillation column is in the range from 50 to 100° C. If there are two or more distillation columns, the distillation columns may be operated at the same or different temperature.

A further parameter for the design of distillation columns is the reflux ratio. The reflux ratio means the ratio of reflux (recyclate) to distillate (withdrawn condensate, in this case therefore the tops stream K). The reflux is thus a condensed portion of the tops stream that is returned to the distillation column. It is preferable in accordance with the invention when the reflux ratio of the at least one distillation column in the distillation in step a. is in the range from 5 to 15.

The distillation according to the invention in step a affords a tops stream K on the at least one distillation column which contains at least 85% by weight of 2,4,4-trimethylpent-1-ene, preferably at least 90% by weight of 2,4,4-trimethylpent-1-ene, preferably at least 95% by weight of 2,4,4-trimethylpent-1-ene. The distillation further affords a stream B which is depleted of 2,4,4-trimethylpent-1-ene relative to stream A.

The stream B additionally obtained in the distillation in step a. may be withdrawn from the at least one distillation column as a bottoms stream or as a side stream. If two distillation columns are present, stream B will be obtained in the last distillation column, irrespective of whether it is withdrawn as a side stream or a bottoms stream. If stream B is withdrawn as a side stream, this may in principle be arranged at the same height or below the inlet for stream A. It will be apparent here that the inflow and outflow must be arranged an adequate distance apart. Stream B, irrespective of whether it is withdrawn as a side stream or bottoms stream, preferably contains 80% to 92% by weight of 2,4,4-trimethylpent-2-ene.

If stream B is withdrawn as a bottoms stream of the at least one distillation column in the distillation in step a. a purge stream containing high-boilers formed during the isomerization, for example dimers or oligomers of 2,4,4-trimethylpent-2-ene and/or 2,4,4-trimethylpent-1-ene, is preferably withdrawn from stream B before or after the isomerization. The removed high boilers can be incinerated to generate energy or can undergo hydrogenation to produce valuable alkanes.

If stream B is withdrawn as a side stream of the at least one distillation column in the distillation in step a, a stream containing the high boilers formed during the isomerization, for example dimers or oligomers of 2,4,4-trimethylpent-2-ene and/or 2,4,4-trimethylpent-1-ene, is preferably obtained in the bottom of the at least one distillation column. The removed high boilers can be incinerated to generate energy or can undergo hydrogenation to produce valuable alkanes.

Distillation columns are, as is known, heated in the column bottom to accomplish the separation task. It is possible here to supply energy via heating steam, which is often available at chemical production sites. This is done by passing a portion of the bottoms through a heat exchanger (reboiler), heating them there and then returning them to the bottom of the distillation column. To reduce energy requirements and/or $CO_2$ emissions a thermal integration may be provided in the distillation in step a. Thermal integration means that energy produced or present within the process is used elsewhere. In the present case, the (released) condensation energy arising at the top of at least one distillation column of the distillation unit is particularly suitable. In a preferred embodiment of the present invention a thermal integration is thus performed in step a. in such a way that at least a portion of the condensation energy at the column top is utilized for heating the bottoms.

Another option for thermal integration is what is known as vapour compression, in which at least a portion of the vapour (tops stream) is compressed, i.e. pressurized to a higher level and optionally heated. The vapour thus compressed and optionally heated is supplied to the heat exchanger (reboiler) in order to heat the bottoms. This makes use of the heat of condensation of the vapour.

A further option is the use of a heat pump. Heat pumps are operated using a working medium such as n-butane or water. The condensation energy is in this case thus first transferred in a heat exchanger to a working medium and from there, in a further suitable heat exchanger, to the distillation bottoms. The working medium is here usually conveyed via a compressor to the heat exchanger in the bottoms. It is in principle also possible to employ two-stage or multistage heat pumps that have more than one compressor stage. In the case of a two-stage heat pump, there is not just one working medium, but two working media, wherein an exchange of energy between the first and the second working medium also takes place in a heat exchanger. In the case of multistage configurations, correspondingly more working media are present.

The isomerization in step b. is performed with stream B which is depleted in 2.4,4-trimethylpent-1-ene relative to stream A and is removed from the distillation in step a. In addition to stream B the input stream may be partially or completely sent to the isomerization.

The isomerization may in principle still be performed in any suitable reactor. It is possible for the isomerization to take place in a single reactor or in two or more reactors connected in parallel or in series. Performance in batches or in continuous operation is also possible. The isomerization is preferably carried out in one or more continuously operated reactors that are customarily employed in solid/liquid contact reactions. When using continuously operated flow reactors, a fixed bed is usually, but not always, employed. When a fixed-bed flow reactor is used, the liquid can flow in an upward or downward direction. In most cases, downward flow of the liquid is preferable. In addition, it is possible to operate the reactor with product recycling or in straight pass. A concept distinct from fixed bed reactors is represented for example by reactors in which the ion exchanger or zeolite is suspended in a liquid phase.

Reactors employed in the isomerization according to the invention are preferably tubular reactors or tube bundle reactors, in particular those having internal tube diameters of 10 to 60 mm. The length-to-diameter ratio of the catalyst bed may be varied here, either by the geometric dimensions of the reactor or by its fill level. At the same contact amount and load (LHSV), it is thus possible to achieve different empty-tube velocities and to selectively influence the heat transfer to the cooling medium.

The cooling of the tubes of the reactor, whether it be a tubular reactor or a tube bundle reactor, can be effected via a cooling medium (for example cooling water or a heat-absorbing process fluid for thermal integration) via the shell space of the reactor or a heat exchanger in an external recycling system. Especially when using liquid heating media, the shell side is constructed such that the temperature gradient in contact with all tubes is as homogeneous as possible. The technical measures necessary for this are known to those skilled in the art and are described in the literature (installation of baffle plates, disc-on-donut construction, infeed/outfeed of heat-transfer medium at various points in the reactor, etc.). Preferably, the reaction medium and heat transfer medium are respectively conveyed through the reactor tubes and reactor jacket in cocurrent flow, more preferably from top to bottom. A preferred embodiment is described for example in DE 10 2006 040 433 A1.

The isomerization of 2,4,4-trimethylpent-2-ene to 2,4,4-trimethylpent-1-ene takes place exothermically, i.e. it proceeds with the release of energy, which results in warming of the reaction mixture. The temperature rise may be limited by diluting the input stream, for example by recycling product.

The reactor(s) used in the isomerization may be operated adiabatically, polytropically or practically isothermally. Practically isothermally means that the temperature is at no point in the reactor more than 10° C. higher than the temperature at the reactor entrance. In the case of adiabatic operation of the reactors, it is usually advantageous to arrange a plurality of reactors in series and to provide cooling between the reactors. Reactors that are suitable for polytropic or practically isothermal operation are for example the tube bundle reactors already mentioned and also stirred-tank reactors and loop reactors.

The process can be executed at rather mild temperatures. The isomerization in step b is preferably performed at a temperature of 25° C. to 90° C., preferably 30° C. to 80° C., particularly preferably 35° C. to 70° C.

In addition, the isomerization of the invention can be carried out at a pressure equal to or greater than the vapour pressure of the input stream mixture and/or of the reaction mixture at the respective reaction temperature, preferably at a pressure of more than 0 bar but less than 40 bar.

The isomerization in step b. is preferably also performed in the liquid phase. It should be clear that in this case the pressure and temperature must be chosen such that the input stream is present, or may be present, in the liquid phase.

The isomerization according to the invention may also employ different catalysts based on a zeolite or an ion-exchange resin in the reactor(s). For example, a mixture of ion-exchange resins of different reactivity may be used. It is likewise possible for a reactor to contain catalysts of different activities that are arranged for example in layers. If more than one reactor is used, the individual reactors may be filled with the same or different catalyst(s) based on a zeolite or on an ion-exchange resin.

The isomerization according to the invention employs a catalyst based on a zeolite or an ion-exchange resin as the heterogeneous catalyst. Appropriate zeolites and ion-exchange resins are widely available and known to those skilled in the art. It has been found that the catalyst based on a zeolite preferably has a Si:Al ratio in the range from 40:1 to 200:1. In the case of catalysts based on an ion-exchange resin, preferably the styrene-divinylbenzene type as the H-form and in a partially neutralized form has in addition been found to be highly suitable.

When the catalyst is a zeolite, some zeolites have proven to be particularly advantageous, for example beta- and gamma-zeolites. The zeolite is therefore preferably selected from the group consisting of Z-beta-H-25, Z-beta-H-38, Z-beta-H-360, Z-Mor-H-20, Z-Y-H-60, Z-Y-H-80, Z-beta-H, Z-CFG-1, Z-beta-ammonium-38, Z-CBV 760 CY (1.6), Z-CBV 780 CY (1.6), CP 814E CY (1.6), CBV 500 CY (1.6), H-CZB-150 and mixtures thereof.

The ion-exchange resin employed may be for example ion-exchange resins produced by sulfonation of phenol/aldehyde condensates or by sulfonation of copolymers of aromatic vinyl compounds. Examples of aromatic vinyl compounds for the production of the copolymers are: styrene, vinyltoluene, vinylnaphthalene, vinylethylbenzene, methylstyrene, vinylchlorobenzene, vinylxylene and divinylbenzene. Particular preference is given to using for the isomerization ion-exchange resins produced by the sulfonation of copolymers formed by the reaction of styrene with divinylbenzene. The ion-exchange resins may be produced in gel-like, macroporous or sponge-like form. The properties of these resins, in particular specific surface area, porosity, stability, swelling or shrinkage and exchange capacity may, as is known, be varied via the production process.

Ion-exchange resins of the preferred styrene-divinylbenzene type are sold inter alia under the following trade names: CT 151 and CT275 from Purolite, Amberlyst® 15, Amberlyst® 35, Amberlite® IR-120, Amberlite® 200 from Rohm&Haas, Dowex M-31 from Dow, Lewatit® K 2621, Lewatit® K 2431 from Lanxess.

The pore volume of the ion-exchange resins employable as catalysts, in particular those of the preferred styrene-divinylbenzene type, is preferably 0.3 to 0.9 ml/g, more preferably 0.5 to 0.9 ml/g. The pore volume can be determined for example by adsorptive techniques. The particle size of the ion-exchange resins is preferably from 0.3 mm to 1.5 mm, more preferably 0.5 mm to 1.0 mm. A narrower or broader particle size distribution may be chosen. It is thus possible for example to use ion-exchange resins having a very uniform particle size (monodisperse resins).

The ion-exchange resins employable as catalysts for the isomerization may be present as partially neutralized ion-exchange resins. For this purpose, the ion-exchange resin may be treated with acids or bases, as described in EP 1 360 160 B1.

The isomerization in step b. then affords a product stream having a proportion of the 2,4,4-trimethylpent-2-ene which is lower and a proportion of the 2,4,4-trimethylpent-1-ene which is higher than in the employed stream B. The product stream from the isomerization is then partially or completely sent to the distillation in step a.

Figure 1:
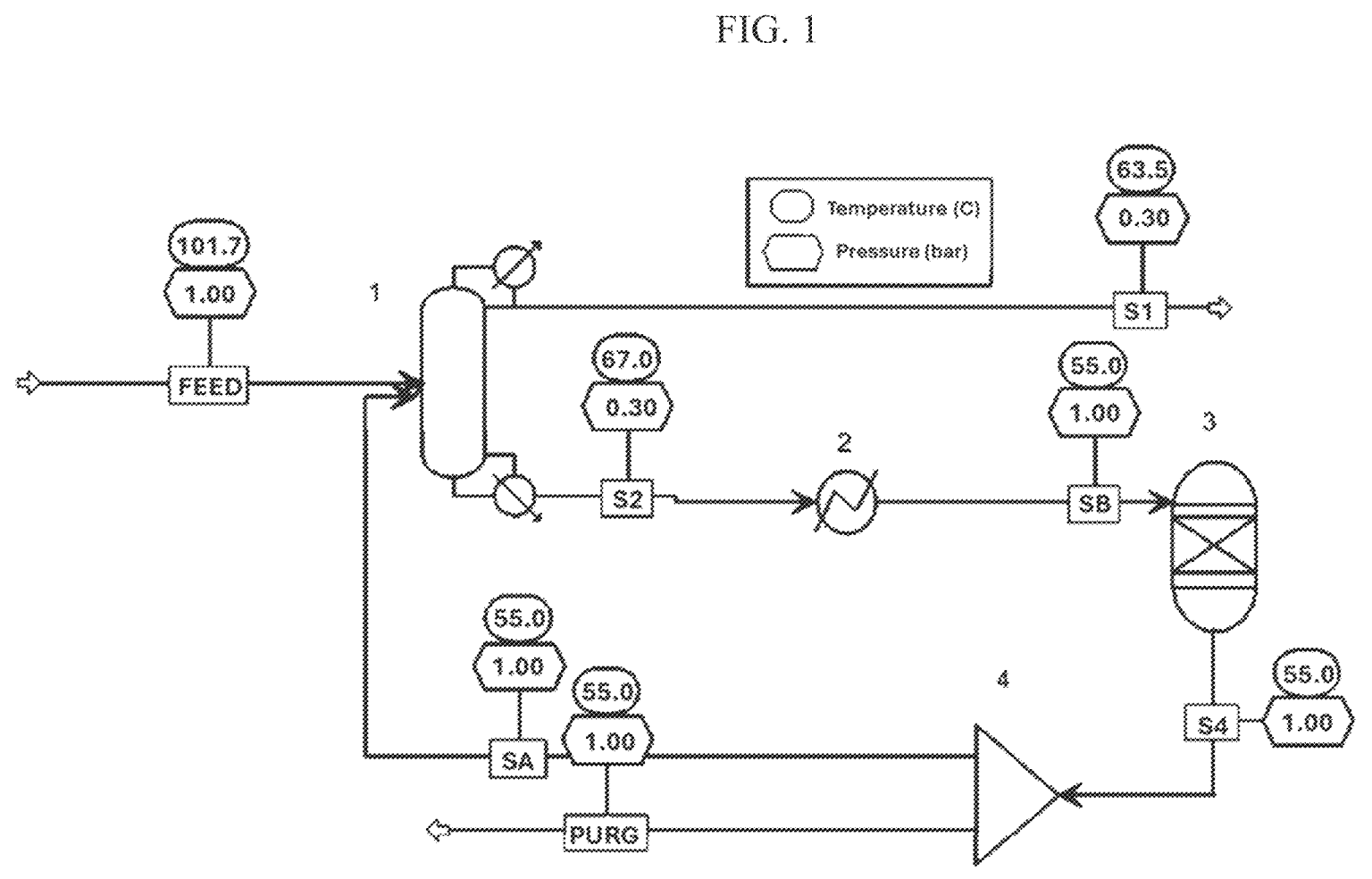
Figure 3:
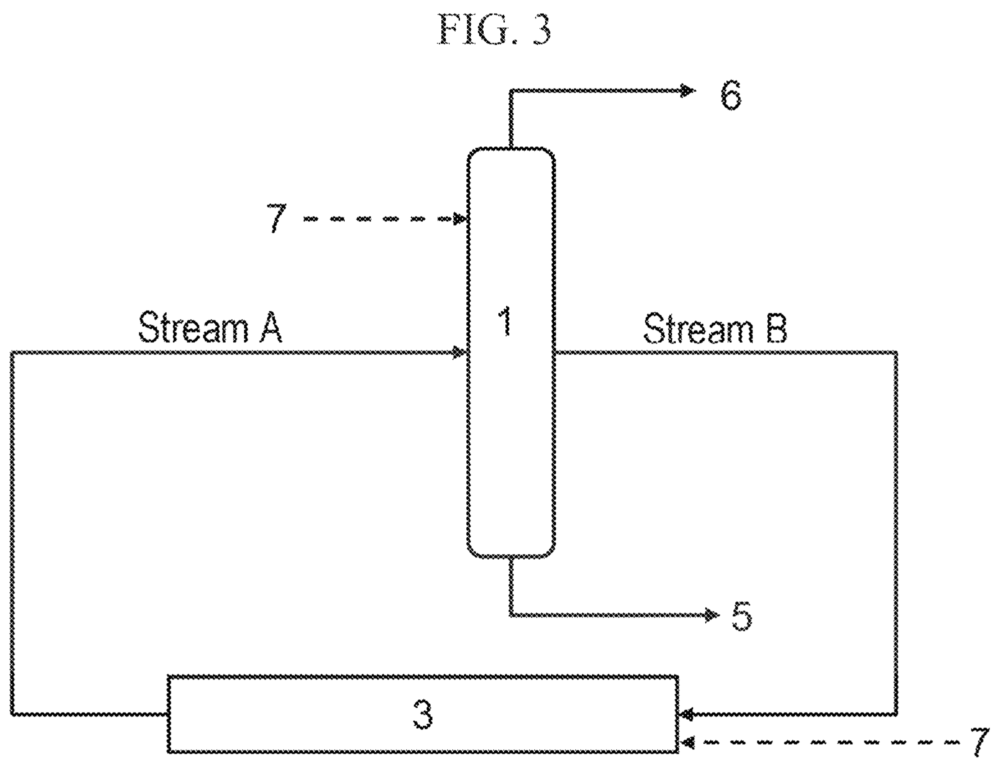
FIG. 3 shows the embodiment in which stream B is withdrawn from the distillation (1) as a side stream.
Figure 4:
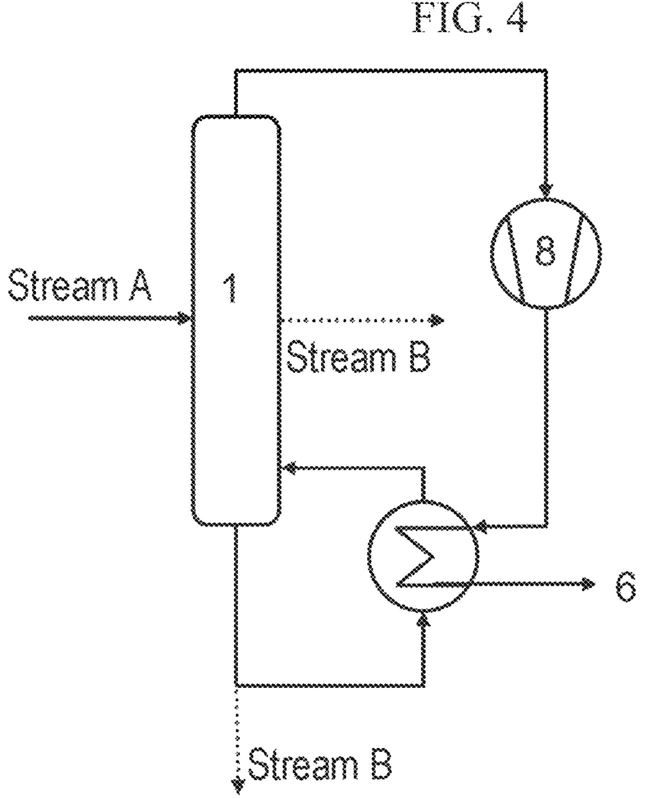
FIG. 4 shows a section of the embodiments shown in FIGS. 2 and 3, wherein, in contrast to these embodiments, a vapour compression is present here.

The present invention may be more particularly elucidated with reference to the figures FIG. 2, FIG. 3 and FIG. 4. FIG. 1 shows the flow diagram on which the simulations in example 2 have been based and which is explained in the experimental description.

FIG. 2 shows the embodiment in which stream B is withdrawn from the distillation (1) as a bottoms stream. Stream B is then sent to the isomerization (3). The product stream obtained there is sent to the distillation (1). A purge stream (5) may be withdrawn before or after the isomerization (3) in case of formation of high boilers. This is indicated by the dashed lines. Separation of high boilers before the isomerization is more advantageous. The distillation (1) and/or the isomerization (3) are also fed with the input stream (7). The desired tops stream K (6) is then withdrawn from the distillation.

FIG. 3 shows the embodiment in which stream B is withdrawn from the distillation (1) as a side stream. In this embodiment, any high boilers obtained will be obtained in the bottoms of the distillation (1) as purge (5). Everything else is identical to the embodiment according to FIG. 2.

FIG. 4 shows a section of the embodiments shown in FIGS. 2 and 3, wherein, in contrast to these embodiments, a vapour compression is present here. The vapour is sent to the bottoms via the compressor (8) and energy is transferred to the bottoms in the heat exchanger. The vapour (6) is condensed and discharged from the process as a TMP-1-rich fraction. In the case of stream B, the options for withdrawal of the stream from the distillation described in FIGS. 2 and 3 are indicated by dashed lines.

The invention is described hereinbelow by reference to examples. These are provided for elucidation purposes and do not limit the subject matter of the invention.

EXAMPLES

Example 1

2.4 g of a catalyst according to the invention (Purolite CT 275, partially neutralized, 0.9 eq/L) were weighed into a tubular reactor having a diameter of 0.6 cm and a height of 12 cm. This results in an empty-tube volume of 3.39 $cm^3$. The reactor was supplied with 2,4,4-trimethylpent-2-ene (>99%) at a flow rate of 0.1 g/min. This results in an empty-tube residence time of 24.5 min. The isomerization was carried out at a temperature of 55° C. and ambient pressure. After exiting the reactor the distribution of 2,4,4-trimethylpent-2-ene to 2,4,4-trimethylpent-1-ene was determined (in the input stream 2,4,4-trimethylpent-2-ene: 2,4,4-trimethylpent-1-ene 99:1), as shown in Table 1. Analysis was by gas chromatography. Peak areas were evaluated by the external calibration method.

TABLE 1

| Proportion of isomers in the diisobutene | | | |
|---|---|---|---|
| Mass stream of 2,4,4-trimethylpent-2-ene [g/min] | Temperature [° C.] | w fraction of 2,4,4-trimethylpent-2-ene in diisobutene isomers in product stream [%] | w fraction of 2,4,4-trimethylpent-1-ene in diisobutene isomers in product stream [%] |
| 0.1 | 55 | 22[a] | 78[a] |

[a]Over experimental duration of 80 hours.

The results show that the catalyst according to the invention is very suitable for the isomerization.

Example 2

Material data available within Evonik were used for the simulation. Aspen Plus version V10 was used as the simulation tool. The isomerization reactor was specified according to the experimental data from example 1 (Purolite CT 275, partially neutralized, 0.9 eq/L). FIG. 1 accordingly shows a process in which diisobutene is initially distillatively separated into 2,4,4-trimethylpent-1-ene and 2,4,4-trimethylpent-2-ene to convert the stream enriched in TMP2 at the column bottom back into a stream enriched in TMP1 over a heterogeneous catalyst and then send this back to the distillative separation to afford a product stream enriched in TMP1.

The input stream "FEED" consists of a mixture of TMP1 and TMP2 in a ratio of 81% by weight TMP1 and 19% by weight TMP2. This is supplied via plate 50 to the distillation column (1) operated with 100 theoretical plates at a reflux ratio of 8. The distillation column (1) is operated at 0.3 bar and at a column-bottom temperature of 67° C. and a column-top temperature of 65.3° C. The stream S2 is obtained at the column bottom at 67° C. and with a composition of 9.13% by weight TMP1 and 90.87% by weight TMP2, cooled to 55° C. via heat exchanger (2) and supplied to the isomerization reactor (3) as stream B. The isomerization reactor (3) is filled with a heterogeneous catalyst (as mentioned in example 1). An empty-tube residence time of >24 min results in stream S4 with a composition of 78% by weight TMP1 and 22% by weight TMP2. If a purge is necessary this stream may be split into stream PURGE and stream A via a splitter (4) (factor 0.03). Stream A is returned to the distillation column (1) above plate 40. At the top of the distillation column (1) the fully condensed tops stream K is obtained at a temperature of 63.5° C., the stream having a composition of 96% by weight TMP1 and 4% by weight TMP2. An overview of the composition of the streams may also be found in table 2.

TABLE 2

Overview of the individual streams for the simulation in example 2

| | Units | FEED | Stream A (SA) | Tops stream K | S2 | Stream B (SB) | S4 |
|---|---|---|---|---|---|---|---|
| Phase | | Liquid | Liquid | Liquid | Liquid | Liquid | Liquid |
| Temperature | ° C. | 101.7 | 55 | 63.5 | 67 | 55 | 55 |
| Pressure | bar | 1 | 1 | 0.3 | 0.3 | 1 | 1 |
| | | | | Mass fraction | | | |
| TMP1 | | 0.81 | 0.78 | 0.96 | 0.09 | 0.09 | 0.78 |
| TMP2 | | 0.19 | 0.22 | 0.04 | 0.91 | 0.91 | 0.22 |

It is apparent that the process according to the invention makes it possible to obtain a tops stream K having a very high content of 2,4,4-trimethylpent-1-ene.

The invention claimed is:

1. A process for providing a tops stream K containing more than 85% by weight of 2,4,4-trimethylpent-1-ene, wherein the process comprises:

a) supplying a stream A containing 2,4,4-trimethylpent-2-ene (TMP-2) and 2,4,4-trimethylpent-1-ene (TMP-1) to a distillation unit and separating the stream A into at least the tops stream K enriched in 2,4,4-trimethylpent-1-ene relative to stream A and containing more than 85% by weight of 2,4,4-trimethylpent-1-ene and a stream B which is depleted in 2,4,4-trimethylpent-1-ene relative to stream A and contains 80% to 92% by weight of 2,4,4-trimethylpent-2-ene;

b) performing an isomerization of 2,4,4-trimethylpent-2-ene to 2,4,4-trimethylpent-1-ene with stream B using a heterogeneous catalyst based on a zeolite or an ion-exchange resin to obtain a product stream of the isomerization in which a proportion of 2,4,4-trimethylpent-2-ene is lower and a proportion of 2,4,4-trimethylpent-1-ene is higher than in stream B;

wherein the product stream of the isomerization is at least partially sent to the distillation as stream A, and wherein an input stream with which the process is fed and which is obtained from dimerization of isobutene, wherein the input stream consists essentially of 2,4,4-trimethylpent-2-ene and 2,4,4-trimethylpent-1-ene, wherein the input stream has a mass distribution of TMP1:TMP2 of about 78:22 to 81:19, and wherein the input stream is distinct from stream A and stream B, is sent to the distillation unit in a) in addition to stream A or to the isomerization in b) in addition to stream B.

2. The process according to claim 1, wherein the distillation unit comprises at least one distillation column.

3. The process according to claim 2, wherein the at least one distillation column is operated at subatmospheric pressure.

4. The process according to claim 2, wherein a temperature in a bottom of the at least one distillation column is in a range from 50° C. to 100° C.

5. The process according to claim 2, wherein a reflux ratio for the at least one distillation column is 5 to 15.

6. The process according to claim 2, wherein stream B is withdrawn from the at least one distillation column as a bottoms stream or as a side stream.

7. The process according to claim 5, wherein stream B is withdrawn as a bottoms stream of the at least one distillation column and a purge stream containing high boilers formed during the isomerization is withdrawn before or after the isomerization.

8. The process according to claim 5, wherein stream B is withdrawn as a side stream of the at least one distillation column and a stream containing high boilers formed during the isomerization is obtained in the bottom of the at least one distillation column.

9. The process according to claim 1, wherein the isomerization in b) is performed at a temperature of 25° C. to 90° C.

10. The process according to claim 1, wherein the zeolite is used and has a Si:Al ratio in a range from 40:1 to 200:1.

11. The process according to claim 1, wherein the zeolite is used and is selected from the group consisting of beta- and gamma-zeolites.

12. The process according to claim 1, wherein the catalyst is a zeolite and is selected from the group consisting of Z-beta-H-25, Z-beta-H-38, Z-beta-H-360, Z-Mor-H-20, Z-Y-H-60, Z-Y-H-80, Z-beta-H, Z-CFG-1, Z-beta-ammonium-38, Z-CBV 760 CY (1.6), Z-CBV 780 CY (1.6), CP 814E CY (1.6), CBV 500 CY (1.6), H-CZB-150 and mixtures thereof.

13. The process according to claim 1, wherein the ion-exchange resin is employed and is selected from the group consisting of ion-exchange resins produced by sulfonation of phenol/aldehyde condensates and ion-exchange resins produced by sulfonation of copolymers of aromatic vinyl compounds.

14. The process according to claim 2, wherein a thermal integration is performed in a) in such a way that at least a portion of condensation energy at a top of the at least one distillation column is utilized for heating the bottoms.

15. The process according to claim 1, wherein the distillation unit comprises at least two distillation columns.

16. The process according to claim 2, wherein the at least one distillation column is operated at a pressure of 0.2 to 0.9 bar.

17. The process according to claim 1, wherein the isomerization in b) is performed at a temperature of 35° C. to 70° C.

18. The process according to claim 2, wherein a thermal integration is performed in a) in such a way that at least a portion of condensation energy at a top of the at least one distillation column is utilized for heating the bottoms in the form of a vapour compression or through the use of a heat pump.

19. The process according to claim 1, wherein the input stream is sent to the distillation unit in a) in addition to stream A.

20. The process according to claim 1, wherein the input stream is sent to the distillation unit in a) in addition to stream A and to the isomerization in b) in addition to stream B.

* * * * *